United States Patent [19]
Seibel et al.

[11] Patent Number: 5,096,700
[45] Date of Patent: Mar. 17, 1992

[54] HALOGENATED AMINOHEXANOATES AND AMINOBUTYRATES ANTIMICROBIAL AGENTS

[75] Inventors: William L. Seibel, Fairfield; Joseph H. Gardner, Cincinnati, both of Ohio

[73] Assignee: The Procter & Gamble Company, Cincinnati, Ohio

[21] Appl. No.: 590,427

[22] Filed: Sep. 28, 1990

[51] Int. Cl.$^5$ .................... A61K 7/18; C07C 229/00; C07C 233/00

[52] U.S. Cl. ........................................ 424/52; 424/54; 548/344; 548/496; 548/535; 560/39; 560/41; 560/153; 560/169; 560/172; 562/448; 562/449; 562/556; 562/561; 562/564; 562/567; 562/574; 564/154; 564/155; 564/157; 564/158; 564/159; 514/400; 514/419; 514/423; 514/542; 514/550; 514/561; 514/562; 514/563; 514/616

[58] Field of Search .................. 560/172, 169, 39, 41, 560/153; 562/561, 574, 448, 449, 556, 564, 567; 514/550, 561, 400, 419, 423, 542, 562, 563, 616; 424/52, 54; 548/344, 496, 535; 564/154, 155, 157, 158, 159

[56] References Cited

U.S. PATENT DOCUMENTS

| | | | |
|---|---|---|---|
| 3,038,003 | 6/1962 | Furst | 560/172 |
| 3,966,796 | 6/1976 | Kaminski et al. | 260/482 R |
| 4,028,405 | 6/1977 | Kollonitsch et al. | 260/534 C |
| 4,045,578 | 8/1977 | Kaminski et al. | 424/311 |
| 4,309,342 | 1/1982 | Chu et al. | 260/112.5 R |
| 4,386,103 | 5/1983 | Pogany et al. | 424/313 |
| 4,418,077 | 11/1983 | Bey | 562/561 |
| 4,727,062 | 2/1988 | Taub et al. | 514/18 |
| 4,730,006 | 3/1988 | Bohme et al. | 514/538 |
| 4,806,680 | 2/1989 | Taub et al. | 562/574 |

OTHER PUBLICATIONS

Goodacre, J., L. Jeffries, J. H. C. Nayler, R. J. Ponsford & I. Sterling, "Antibacterial Halogenoacetyl Derivatives of Amino Acids and Simple Peptides", *Journal of Medicinal Chemistry*, vol. 20, No. 11 (1977), pp. 1445–1448.

Johnston, M., P. Marcotte, J. Donovan & C. Walsh, "Mechanistic Studies with Vinylglycine and β-Haloaminobutyrates as Substrates for Cystathionine γ-Synthetase from Salmonella typhimurium", Biochemistry, vol. 18, No. 9 (1979), pp. 1729–1738.

Tolman, V., & J. Benes, "Monofluorinated Analogs of Some Aliphatic Basic Amino Acids", *Journal of Fluorine Chemistry*, vol. 7 (1976), pp. 397–407.

*Primary Examiner*—Michael L. Shippen
*Attorney, Agent, or Firm*—Milton B. Graff, IV; Jerry J. Yetter; Richard C. Witte

[57] ABSTRACT

The subject invention involves halogenated amino acid derivatives useful as antimicrobial agents having the structure:

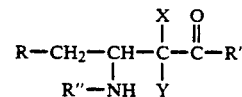

wherein —R is hydrogen or 2-aminoethyl; —R' is hydroxy, alkoxy, aryloxy, or an amino acid residue bonded at the amino nitrogen; —R" is hydrogen or an amino acid residue bonded at the carbonyl carbon; —X is halogen; and —Y is hydrogen or halogen.

11 Claims, No Drawings

HALOGENATED AMINOHEXANOATES AND AMINOBUTYRATES ANTIMICROBIAL AGENTS

TECHNICAL FIELD

The present invention relates to novel halogenated amino acid derivatives useful as antimicrobial agents.

BACKGROUND OF THE INVENTION

There are many known uses for antimicrobial agents, for cleaning, sterilizing, and for preventing and treating many diseases. Because bacteria are often able to develop resistant strains to antimicrobial agents, there is a continual need for the development of new antimicrobial compounds.

Certain halogenated amino acid derivatives having anti-microbial activity are known. The following references disclose such compounds: U.S. Pat. Nos. 3,966,796 and 4,045,578 issued to Kaminski & Bodor on June 29, 1976 and Aug. 30, 1977, respectively; 4,028,405 issued to Kollonitsch & Kahan June 7, 1977; 4,309,342 issued to Chu, Martin & Thomas on Jan. 5, 1982; 4,386,103 issued to Pogany & Higuchi on May 31, 1983; 4,727,062 and 4,806,680 issued to Taub, Abeles & Patchet on Feb. 23, 1988 and Feb. 21, 1989, respectively; 4,730,006 issued to Bohme, Gerhart & Higgins on Mar. 8, 1988; Tolman, V. & J. Benes, "Monofluorinated Analogs of Some Aliphatic Basic Amino Acids", *Journal of Fluorine Chemistry*, Vol. 7 (1976), pp. 397-407; Goodacre, J., L. Jeffries, J. H. C. Nayler, R. J. Ponsford & I. Sterling, "Antibacterial Halogenoacetyl Derivatives of Amino Acids and Simple Peptides", *Journal of Medicinal Chemistry*, Vol. 20, No. 11 (1977), pp. 1445-1448; Johnston, M., P. Marcotte, J. Donovan & C. Walsh, "Mechanistic Studies with Vinylglycine and β-Haloaminobutyrates as Substrates for Cystathionine γ-Synthetase from *Salmonella typhimurium*", *Biochemistry*, Vol. 18, No. 9 (1979), pp. 1729-1738.

It is an object of the subject invention to provide novel halogenated amino acid derivatives useful as antimicrobial agents.

It is a further object of the subject invention to provide such novel antimicrobial agents having selective anaerobic anti-bacterial activity.

It is also an object of the subject invention to provide methods for treating diseases caused by anaerobic bacteria.

SUMMARY OF THE INVENTION

The subject invention involves antimicrobial compounds having the following structure:

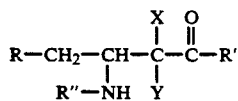

wherein —R is hydrogen or 2-aminoethyl; —R' is hydroxy, alkoxy, aryloxy, or an amino acid residue bonded at the amino nitrogen; —R" is hydrogen or an amino acid residue bonded at the carbonyl carbon; —X is halogen; and —Y is hydrogen or halogen.

The subject invention also involves pharmaceutical compositions comprising the above compounds, and methods for treating or preventing anaerobic bacterial diseases.

DETAILED DESCRIPTION OF THE INVENTION

The term "alkyl", as used herein, means carbon-containing chains which may be straight, branched, or cyclic; and which may be saturated, monounsaturated (i.e., one double or triple bond in the chain), or polyunsaturated (e.g., two double bonds in the chain, two triple bonds in the chain, one double and one triple bond in the chain). Preferred alkyl are as noted in this paragraph, unless provided otherwise in particular instances. Alkyl groups may be substituted or, preferably, unsubstituted. Preferred substituents are selected from the group consisting of halogen, hydroxy, amino, aryl, heteroaryl, carboxylate, and alkoxy. It is preferred that substituted alkyl groups be mono-, di- or trisubstituted, especially monosubstituted. Alkyl are preferably $C_1$-$C_{20}$, more preferably $C_1$-$C_{12}$, more preferably still $C_1$-$C_6$, still more preferably $C_1$-$C_3$, most preferably $C_1$. Preferred alkyl are straight-chain. As used herein, "alkoxy" is —O-alkyl.

The term "aryl", as used herein, means aryl rings which may be mono-, di-, tri-, or unsubstituted, preferably monosubstituted or unsubstituted, especially unsubstituted. Preferred aryl is as noted in this paragraph, unless provided otherwise in particular instances. Preferred aryls include unsubstituted and substituted phenyl and naphthyl. Most preferred aryl is unsubstituted or substituted phenyl. Preferred substituents include halogen, hydroxy, alkoxy, amino, nitro, cyano, phenyl, benzyl, benzyloxy, trifluoromethyl, formylamino, carboxy and alkyl; more preferred substituents include trifluoromethyl, carboxyl and alkyl. As used herein, "aryloxy" is —O-aryl.

The term "amino acid", as used herein, means natural and synthetic amino acids. Natural amino acids which are commonly present in the proteins of plants and animals are preferred and include: glycine, alanine, valine, leucine, isoleucine, serine, threonine, proline, hydroxyproline, phenylalanine, tyrosine, tryptophan, cystine, cysteine, methionine, histidine, arginine, lysine, hydroxylysine, aspartic acid, glutamic acid, asparagine and glutamine. Other amino acids include, but are not limited to: b-alanine, γ-aminobutyric acid, α-aminobutyric acid, α-aminoisobutyric acid, sarcosine, 2-carboxy-azetidine, 2-carboxyl-th dine, pipecolinine, 2,3-dehydroproline, β-(2-thienyl)alanine, β-(1-naphthyl)alanine, β-(2-naphthyl)alanine, β-(2-peridyl)alanine, p-nitrophenylalanine, p-chlorophenylanaline, o-methyltyrosine, homophenylalanine, α-phenylglycine, homoarginine, homoserine, ornithine, 4-carboxyproline, 4-carbamoylproline, N-acetyl-4-aminoproline, N-acetylornithine, N-hydroxyasparagine, N-hydroxyglutamine, citrulline, and dihydroxyphenylalanine. Amino acids, except for glycine, occur as l- and d-stereoisomers. Preferred amino acids are l-isomers.

The term "amino acid residue", as used herein, means an amino acid which is bonded to other constituents within a chemical structure. The amino acid is preferably bonded at either or both of the amine nitrogen and the carbonyl carbon of the amino acid, as is typical for the amino acids as residues of a polypeptide.

The novel antimicrobial compounds of the subject invention are those having the following chemical structure:

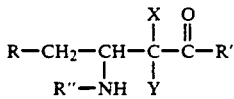

wherein —R is hydrogen or 2-aminoethyl; —R' is hydroxy, alkoxy, aryloxy, or an amino acid residue bonded at the amino nitrogen; —R" is hydrogen or an amino acid residue bonded at the carbonyl carbon; —X is halogen; and —Y is hydrogen or halogen.

When —R' is alkoxy or aryloxy, preferred alkyl or aryl portions of the substituent are as defined for those terms hereinbefore. When —R' is an amino acid residue, it is preferably selected from the group consisting of natural α-1-amino acids or racemic mixtures thereof; more preferably from the group consisting of glycyl, alanyl, arginyl, asparagyl, ornithyl, phenylalanyl, prolyl, sarcosyl, seryl, threonyl, tryptophyl, tyrosyl and valyl; most preferably R' is glycyl.

When —R" is an amino acid residue, it preferably is selected from the group consisting of natural α-1-amino acids or racemic mixtures thereof; more preferably from the group consisting of glycyl, alanyl, arginyl, asparagyl, ornithyl, phenylalanyl, prolyl, sarcosyl, seryl, threonyl, tryptophyl, tyrosyl and valyl; most preferably —R" is glycyl.

—X and —Y (when halogen) are each independently selected from fluorine, chlorine, bromine and iodine, preferably from fluorine and chlorine, more preferably fluorine.

Preferred compounds of the subject invention include di- and tripeptides incorporating 3-amino-2-halobutanoic acid, 3,6-diamino-2-halohexanoic acid, 3-amino-2,2-dihalobutanoic acid, and 3,6-diamino-2,2-dihalohexanoic acid; more preferred compounds include dipeptides incorporating 3-amino-2-fluorobutanoic acid or 3,6-diamino-2-fluorohexanoic acid. Preferred compounds include 3-(2-aminoacetamido)-2-fluorobutanoic acid, N-(3-amino-2-fluorobutanoyl)glycine, and 3,6-diamino-2-fluorohexanoic acid.

Preferred antimicrobial compounds of the subject invention include pharmaceutically-acceptable salts of the above compounds. Preferred salts are metal salts or ammonium-based salts of the above compounds which have a terminal carboxy moiety. Preferred salts include sodium, potassium, ammonium, alkylammonium, dialkylammonium, trialkylammonium, tetraalkylammonium, calcium, magnesium, zinc, copper and tin; more preferred salts include sodium, potassium and zinc. Preferred salts also include salts of addition. Examples of salts of addition include hydrochloride, hydrobromide, acetate, sulfate, phosphate, adipate, citrate, tartrate, succinate, fumarate, oleate, propionate, formate and lactate; preferred salts of addition include hydrochloride and acetate.

The following methods are exemplary of procedures for synthesizing the compounds of the subject invention. They are not intended to be complete or limiting regarding methods of synthesizing the compounds. Skilled chemists will be aware of other processes useful for synthesizing the subject compounds.

EXAMPLE 1

Synthesis of N-(3-(S)-Amino-2-(R)-fluorobutanoyl)glycine

N,N-Dibenzylthreonine benzyl ester:

A suspension of l-threonine (30.0 g, 252 mmol) in dimethylformamide (500 mL) is treated with benzyl bromide (151 g, 882 mmol) and potassium carbonate (113 g, 882 mmol). The mixture is stirred at 60° C. for 18 hours, then poured into ether and water. The ether layer is separated and washed with 1M hydrochloric acid to remove any mono- and dibenzylated products. The organics are dried over magnesium sulfate followed by evaporation of the solvent in vacuo to give the crude product as a deep red oil. The crude material is purified by filtration through a plug of silica gel with 10% ethyl acetate as eluent. The desired compound is obtained as a pale orange oil (60.2 g) which solidifies on standing.

Benzyl 3-(S)-N,N-Dibenzylamino-2-(R)-fluorobutanoate:

A solution of N,N-dibenzylthreonine benzyl ester (60.0 g, 154 mmol) in 500 mL of tetrahydrofuran at 0° C. is treated with diethylaminosulfur trifluoride (28.5 g, 177.2 mmol). A 30 minutes; the reaction is quenched with ice. The solution is diluted with ether and washed with 0.1M hydrochloric acid, water and saturated sodium chloride solution. The solution is dried over magnesium sulfate and concentrated in vacuo. Chromatography of the crude product on silica gel with 3% ethyl acetate/hexanes as eluent affords 35.3 g of pure benzyl 3-(S)-N,N-dibenzylamino-2-(R)-fluorobutanoate and 15 g of the corresponding isomer, benzyl 2-(S)-N,N-dibenzylamino-3-(R)-fluorobutanoate.

N-Benzyloxycarbonyl-3-(S)-amino-2-(R)-fluorobutanoic acid:

Benzyl 3-(S)-N,N-dibenzylamino-2-(R)-fluorobutanoate (26.2 g, 66.8 mmol) in 370 mL of methanol containing 5.6 mL of concentrated hydrochloric acid is connected to a Parr hydrogenation apparatus with 2.62 g of palladium hydroxide as catalyst and hydrogenated in two lots at 50 psi. The lots are combined and filtered through a pad of celite. The celite is washed with water and methanol and the combined filtrates are concentrated in vacuo to give a yellow oil. The crude amino acid is taken up in 290 mL of water and treated with sodium carbonate (15.6 g, 140 mmol) and benzyl chloroformate (12.0 g, 70 mmol). After stirring for 4.5 hours, another 7.8 g of sodium carbonate is added and the reaction allowed to stir an additional 18 hours. The basic solution is washed with ether and then acidified with 500 mL of 1 hydrochloric acid. The resulting mixture is extracted with ether. Drying over magnesium sulfate followed by removal of the ether in vacuo affords 12.7 g of the desired N-benzyloxycarbonyl-3-(S)-amino-2-(R)-fluorobutanoic acid.

Benzyl N-(Benzyloxycarbonyl-3-(S)-amino-2-(R)-fluorobutanoyl)-glycinate:

A solution of N-benzyloxycarbonyl-3-(S)-amino-2-(R)-fluorobutanoic acid (12.7 g, 49.8 mmol) in 255 mL of methylene chloride at −10° C. is treated with triethylamine (5.04 g, 49.8 mmol) and methyl chloroformate (4.71 g, 49.8 mmol). After 20 minutes, a solution of glycine benzyl ester hydrochloride (5.04 g, 49.8 mmol) and triethylamine (5.04 g, 49.8 mmol) in 230 mL of methylene chloride is added. The reaction is stirred for 1 hour at −10° C. and then washed with 1M hydrochloric acid. The solution is dried over magnesium sulfate and then evaported in vacuo to give 18 g of the crude product. The crude material is purified via silica gel chromatography with 7.5% ethyl acetate/methylene chloride as eluent to give 8.57 g of the desired protected dipeptide.

N-(3-(S)-amino-2-(R)-fluorobutanoyl)glycine:

To a solution of benzyl N-(benzyloxycarbonyl-3-(S)-amino-2-(R)-fluorobutanoyl)glycinate (8.50 g, 21.1 mmol) in 200 mL of methanol is added 850 mg of 10% palladium on carbon. The mixture is connected to a Parr hydrogenation apparatus and hydrogenated at 50 psi for 18 hours. The mixture is then filtered through celite to remove the catalyst. Evaporation of the solvent leaves 3.66 g of the desired product as a white solid.

EXAMPLE 2

Synthesis of 3,6-Diamino-2-fluorohexanoic Acid

Benzyl N,N-dibenzylglycinate:

A mixture of potassium carbonate (566 g, 4.09 mole), l-threonine (150 g, 1.26 mole), and benzyl bromide (700 g, 4.09 mole) in 566 mL of water and 1150 mL of dimethylformamide is heated at 65° C. for 20 hours. The reaction is then allowed to cool and then partitioned into ether and water. The ether layer is washed with water, 1M hydrochloric acid, and saturated sodium chloride solution. The solution is then dried over magnesium sulfate and evaporated to give the crude benzylated threonine. The crude material is then connected to a distillation apparatus and heated at 110° C. at 0.1 mm Hg to remove any remaining benzyl bromide or benzyl alcohol. Heating is then gradually increased to 220° C. for 4 hours to effect retroaldol reaction. Filtration of the red-orange material remaining in the pot (310 g) through a short column of silica gel with methylene chloride as eluent removes most of the color to afford the desired product as a light yellow oil (297 g) which solidifies on standing.

Benzyl 6-Azido-2-N,N-dibenzylamino-3-hydroxyhexanoate:

A solution of lithium diisopropylamide (LDA) in tetrahydrofuran is prepared by sequential addition of diisopropylamine (10.4 g, 103 mmol) and a hexane solution of butyllithium (47.9 mL of 2.15M, 103 mmol) to 510 mL of tetrahydrofuran at 0° C. A solution of benzyl N,N-dibenzylglycinate (33.85 g, 98.1 mmol) in 350 mL of tetrahydrofuran is slowly added at −78° C. to the LDA solution and then allowed to stir an additional 15 minutes. A solution of 4-azidobutanal (12.2 g, 108 mmol) in 35 mL of tetrahydrofuran is then added to the enolate solution. After 1 hour, the reaction is quenched with 130 mL of 10% aqueous acetic acid. Following reduction of the solvent volume in vacuo, the mixture is partitioned between water and ether. The ether is then washed with saturated sodium bicarbonate solution, saturated sodium chloride solution and dried over magnesium sulfate. Evaporation of the solvent in vacuo gives the crude product as a dark orange oil. The isomeric alcohol products are separated via silica gel chromatography using 15% ethyl acetate/hexanes as eluent, which affords 11.2 g of the first isomer and 10.2 g of the second isomer in addition to recovered starting material.

Benzyl 6-Azido-3-N,N-dibenzylamino-2-fluorohexanoate:

A solution of benzyl 6-azido-2-N,N-dibenzylamino-3-hydroxyhexanoate (1.00 g, 2.18 mmol) in 10 mL of tetrahydrofuran at 0° C. is treated with diethylaminosulfur trifluoride. After stirring for 45 minutes, the reaction is quenched by addition of 2 g of ice. The reaction is then diluted with ether and washed with water, saturated sodium bicarbonate solution, saturated sodium chloride solution, and dried over magnesium sulfate. Evaporation of the solvents in vacuo leaves the crude product as a light yellow oil which is purified via silica gel chromatography using methylene chloride as eluent to give the desired product (777 mg) as a colorless oil.

3,6-Diamino-2-fluorohexanoic Acid:

To a solution of benzyl 6-azido-3-N,N-dibenzylamino-2-fluorohexanoate (1.0 g, 2.17 mmol) in 30 mL of 2:1 ethanol/tetrahydrofuran is added 4.06 mL of 1M hydrochloric acid and palladium hydroxide (100 mg). This suspension is placed on a Parr hydrogenation apparatus and hydrogenated at 50 psi over 48 hours. The catalyst is filtered from the mixtures and the solvents removed in vacuo to give 506 mg of the desired product as a dihydrochloride salt.

Another aspect of the subject invention is pharmaceutical compositions comprising a compound of the subject invention as described hereinbefore and a pharmaceutically-acceptable carrier. The compounds of the subject invention preferably comprise from about 0.01% to about 99.99% by weight of the pharmaceutical compositions of the subject invention, preferably from about 0.1% to about 90%. Different types of compositions have differing ranges of active compound preferred: for solid dose formulations, preferably from about 10% to about 90%, more preferably from about 50% to about 75%; for oral rinse formulations, preferably from about 0.05% to about 5%, more preferably from about 0.1% to about 1%; for dentifrice formulations, preferably from about 0.01% to about 10%, more preferably from about 1% to about 5%; for lozenge formulations, preferably from about 0.01% to about 15%, more preferably from about 0.1% to about 5%; and for impregnated fiber, strip or tube formulations, preferably from about 0.1% to about 50%, more preferably from about 10% to about 35%.

Pharmaceutically-Acceptable Carrier

The term "pharmaceutically-acceptable carrier", as used herein, means one or more compatible solid or liquid filler diluents or encapsulating substances which are suitable for administration to a human or lower animal. The term "compatible", as used herein, means that the components of the pharmaceutical compositions are capable of being commingled with the compound of the subject invention, and with each other, in a manner such that there is no interaction which would substantially reduce the pharmaceutical efficacy of the pharmaceutical composition under ordinary usage situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers are sugars such as lactose, glucose and sucrose; starches such as corn starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulphate; vegetable oils such as peanut oil, cottonseed oil, sesame oil, olive oil, corn oil and oil of theobroma; polyols such as propolene glycol, glycerine, sorbitol, mannitol, and polyethylene glycol; alginic acid; pyrogen-free water; isotonic saline; phosphate buffer solutions; cocoa butter (suppository base); emulsifiers, such as the Tweens ®; as well as other non-toxic compatible substances used in pharmaceutical formulations. Wetting agents and lubricants such as sodium lauryl sulfate, as well as coloring agents, flavoring agents, excipients, tableting agents, stabilizers, antioxidants, and preservatives, can also be present.

The choice of a pharmaceutically-acceptable carrier to be used in conjunction with the compounds of the subject invention is determined by the way the compound is to be administered. The preferred modes of administering the compounds of the present invention are by injection, perorally and topically, particularly preferred is topical, oral administration.

"Topical, oral carrier", as used herein, denotes a carrier for the halogenated amino acid derivative which results in a composition which is administered topically to the oral cavity, held therein for a period of time, and then is largely expectorated rather than being swallowed. Such compositions include toothpastes, tooth gels, tooth powders, mouthwashes, mouthsprays, prophylaxis pastes, dental treatment solutions, biogels or other sustained release products, and the like.

Components of the topical, oral carrier are suitable for administration to the oral cavity of a human or lower animal and are compatible with one another and the other components, especially the halogenated amino acid derivative, used in an oral composition of the subject invention. The term "compatible" as used herein, means that the components of the compositions are capable of being commingled with one another, in a manner such that there is no interaction which would substantially reduce the efficacy of the oral composition under ordinary use conditions. Preferred topical, oral carriers thus provide the desired characteristics for toothpastes, tooth gels, tooth powders, mouthwashes, mouthsprays, prophylaxis pastes, dental treatment solutions, and the like. The topical, oral carriers of the subject invention comprise components typically used in such compositions which are well known to a skilled practitioner. Such components include, but are not limited to anticaries agents, antiplaque agents, anticalculus agents, dental abrasives, surfactants, flavoring agents, sweetening agents, binders, humectants, thickening agents, buffering agents, preservatives, coloring agents and pigments, ethanol, and water.

Water is an optional component of the topical, oral carriers of the compositions of the subject invention. Water employed in the preparation of commercially suitable compositions should preferably be of low ion content and free of organic impurities. Water preferably comprises from about 2% to about 99%, more preferably from about 20% to about 95% of the compositions of the subject invention. When in the form of toothpastes, the compositions preferably are from about 2% to about 45%, more preferably from about 30% to about 40%, water, while mouthwashes are preferably from about 45% to about 95%, more preferably from to about 90% water.

Dental abrasives useful in the topical, oral carriers of the compositions of the subject invention include many different materials. The material selected must be one which is compatible within the composition of interest and does not excessively abrade dentin. Suitable abrasives include, for example, silicas including gels and precipitates, insoluble sodium polymetaphosphate, hydrated alumina, and resinous abrasive materials.

A class of preferred abrasives for use in the subject compositions is the particulate thermo-setting polymerized resins as described in U.S. Pat. No. 3,070,510 issued to Cooley & Grabenstetter on Dec. 25, 1962. Suitable resins include, for example, melamines, phenolics, ureas, melamine-ureas, melamine-formaldehydes, urea-formaldehydes, melamine-urea-formaldehydes, cross-linked epoxides, and cross-linked polyesters.

Silica dental abrasives are also preferred in the compositions of the subject invention. The silica abrasive polishing material generally has an average particle size ranging between about 0.1 and about 30 microns, preferably between 5 and 15 microns. The abrasive can be precipitated silica or silica gels such as the silica xerogels described in U.S. Pat. No. 3,538,230 issued to Pader & Wiesner on Mar. 2, 1970, and in U.S. Pat. No. 3,862,307 issued to DiGuilio on Jan. 21, 1975. Preferred are the silica xerogels marketed under the tradename Syloid ® by the W. R. Grace & Co., Davison Chemical Division. Preferred precipitated silica materials are those marketed by the J. M. Huber Corporation under the tradename Zeodent ®, particularly the silica carrying the designation Zeodent 119 ®. These silica abrasives are described in U.S. Pat. No. 4,340,583 issued to Wason on July 29, 1982.

Mixtures of abrasives can be used. All of the above patents regarding dental abrasives are incorporated herein by reference.

The total amount of abrasive in dentifrice compositions of the subject invention preferably range from about 10% to about 70% by weight; toothpastes preferably contain from about 10% to about 50% by weight of abrasives. Solution, mouthspray and mouthwash compositions of the subject invention may contain quantities of abrasive as low as 0%.

Flavoring agents are preferred in the topical, oral carriers of the compositions of the subject invention in order to make them more palatable. Typical flavoring agents include menthol, oil of wintergreen, oil of peppermint, oil of spearmint, oil of sassafras, and oil of clove. If subject, flavoring agents are generally included in the subject compositions in amounts of from about 0.04% to about 2% by weight.

Sweetening agents are also preferred in the topical, oral carriers of the compositions of the subject invention in order to make them more palatable. Typical sweetening agents include saccharin salts, dextrose, levulose, thaumatin, aspartame, D-tryptophan, dihydrochalcones, acesulfame and cyclamate salts, especially sodium cyclamate and sodium saccharin. If subject, sweetening agents are generally included in the subject compositions in amounts of from about 0.01% to about 5% by weight.

Another optional component of the topical, oral carriers of the compositions of the subject invention is a humectant. The humectant serves to keep toothpaste compositions from hardening upon exposure to air, and to give mouthwash and toothpaste compositions a moist feel to the mouth. Certain humectants can also impart desirable sweetness of flavor to mouthwash and toothpaste compositions. The humectant, on a pure humectant basis, generally comprises from about 0% to about 70%, preferably from about 5% to about 55%, by weight of the compositions herein. Suitable humectants for use in compositions of the subject invention include edible polyhydric alcohols such as glycerin, sorbitol, xylitol, polyethylene glycol, and propylene glycol, especially sorbitol and glycerin.

Buffering agents are another optional component of the topical, oral carrier of the compositions of the subject invention. The buffering agents serve to retain the pH of the compositions within the preferred range. The buffering agent generally comprises from about 0% to about 10%, preferably from about 0.2% to about 5%, by weight of the compositions herein. Suitable buffering agents for use in compositions of the subject invention include soluble phosphate salts.

Other optional components of the topical, oral carriers of the compositions of the subject invention are preservatives. The preservatives prevent microbial growth in the compositions. Suitable preservatives include methylparaben, propylparaben, benzoates and ethanol. If the preservative is ethanol, it generally comprises from 0% to about 35%, preferably from about 5% to about 15%, of the compositions herein. Other preservatives generally comprise from about 0% to about 5%, preferably from about 0.1% to about 2%, by weight of the compositions herein.

Binders and thickening agents may be used in the topical, oral carriers of the compositions of the subject invention, particularly in toothpaste compositions. Preferred binders and thickening agents include, for example, carrageenan (e.g., Irish moss, Viscarin TP-5 which is an iota carrageenan), cellulose derivatives (e.g., hydroxyethyl cellulose, sodium carboxymethyl cellulose, sodium carboxymethyl hydroxypropyl cellulose), carboxyvinyl polymers (carbomers), natural gums (e.g., gum karaya, gum arabic, gum tragacanth), polysaccharide gums (e.g., xanthan gum), fumed silica, and colloidal magnesium aluminum silicate. If subject, these binders and thickening agents are generally subject in the compositions of the subject invention in amounts of from about 0.1% to about 5%.

Compositions of the subject invention may also contain a surfactant. Suitable surfactants are those which are reasonably stable and preferably form suds through the pH range of the compositions. Surfactants useful as sudsing agents may be soaps, and anionic, nonionic, cationic, zwitterionic and amphoteric organic synthetic detergents, and compatible mixtures thereof. Surfactants of these types are described more fully in U.S. Pat. No. 3,959,458 issued to Agricola, Briner, Granger & Widder on May 25, 1976 and U.S. Pat. No. 3,937,807 issued to Haefele on Feb. 10, 1976, both of which are incorporated herein by reference. Such surfactants are generally subject in the compositions of the subject invention at a level of from about 0% to about 10%. Surfactants may also be used as solubilizing agents to help retain sparingly soluble components, e.g., some flavoring agents, in solutions. Surfactants suitable for this purpose include polysorbates and poloxamers.

The compositions of the subject invention may also comprise an anticaries agent. Preferred anticaries agents are water-soluble fluoride ion sources. Fluoride ions also generally help stabilize pyrophosphate (generally an anticalculus agent) in the oral cavity, thus enhancing the benefits provided by any soluble pyrophosphate included in the compositions. The number of such fluoride ion sources is great and includes those disclosed in U.S. Pat. No. 3,535,421 issued Oct. 20, 1970 to Briner & Widder, incorporated herein by reference. Preferred fluoride ion source materials include: sodium fluoride, potassium fluoride, and sodium monofluorophosphate and mixtures thereof. Sodium fluoride is the preferred fluoride source. The amount of the fluoride ion source in the oral compositions of the subject invention, if subject, is preferably sufficient to provide from about 0.005% to about 0.35%, more preferably from about 0.05% to about 0.3% of fluoride ions in the compositions.

Antimicrobial antiplaque agents can also optionally be subject in the oral compositions of the subject invention, on the condition that they are compatible with the halogenated amino acid derivative. Such agents may include Triclosan, 5-chloro-2-(2,4-dichlorophenoxy)-phenol, as described in *The Merck Index*, 10th ed. (1976), p. 1381; U.S. Pat. No. 3,506,720; and European Patent Application No. 0,251,591 of Beecham Group, PLC, published Jan. 7, 1988. If subject, the antimicrobial antiplaque agents generally comprise from about 0.1% to about 5% by weight of the compositions of the subject invention.

Compositions of the subject invention may also include one or more anticalculus agents, on the condition that they are compatible with the halogenated amino acid derivative. Anticalculus agents which may be useful in the compositions of the subject invention include pyrophosphates or polyphosphates such as those disclosed in U.S. Pat. No. 4,590,066 issued to Parran and Sakkab on May 20, 1986; polyacrylates and other polycarboxylates such as those disclosed in U.S. Pat. No. 3,429,963 issued to Shedlovsky on Feb. 25, 1969 and U.S. Pat. No. 4,304,766 issued to Chang on Dec. 8, 1981, and U.S. Pat. No. 4,661,341 issued to Benedict & Sundberg on Apr. 28, 1987; polyepoxysuccinates such as those disclosed in U.S. Pat. No. 4,846,650 issued to Benedict, Bush & Sundberg on July 11, 1989; ethylenediaminetetraacetic acid as disclosed in British Patent No. 490,384 dated Feb. 15, 1937; nitrilotriacetic acid and related compounds as disclosed in U.S. Pat. No. 3,678,154 issued to Widder & Briner on July 18, 1972; polyphosphonates as disclosed in U.S. Pat. No. 3,737,533 issued to Francis on June 5, 1973, U.S. Pat. No. 3,988,443 issued to Ploger, Schmidt-Dunker & Gloxhuber on Oct. 26, 1976, and U.S. Pat. No. 4,877,603 issued to Degenhardt & Kozikowski on Oct. 31, 1989; all of these patents are incorporated herein by reference. If subject, the anticalculus agents generally comprise from about 0.2% to about 13%, preferably from about 0.4% to about 6% of the compositions of the subject invention.

Preferred compositions of the subject invention are in the form of toothpastes. Components of such toothpastes generally include a dental abrasive (from about 10% to about 50%), a surfactant (from about 0.5% to about 10%), a thickening agen about 0.1% to about 5%) a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%). Such toothpastes may also include one or more of an anticaries agent (from about 0.05% to about 0.3% as fluoride ion), an anticalculus agent (from about 0.1% to about 13%), and an antiplaque agent (from about 0.1% to about 5%).

Other preferred compositions of the subject invention are mouthwashes and mouthsprays. Components of such mouthwashes and mouthsprays include water (from about 45% to about 95%), ethanol (from about 0% to about 25%), a humectant (from about 0% to about 50%), a surfactant agent (from about 0.01% to about 7%), a flavoring agent (from about 0.04% to about 2%), a sweetening agent (from about 0.1% to about 3%), and a coloring agent (from about 0.001 to about 0.5%). Such mouthwashes and mouthsprays may also include one or more of an anticaries agent (from about 0.05% to about 0.3% as fluoride ion), an anticalculus agent (from about 0.01% to about 3%), and an antiplaque agent (from about 0.1% to about 5%).

Other preferred compositions of the subject invention are dental solutions. Components of such dental solutions generally include water (from about 90% to about 99%), preservative (from about 0.01% to about 0.5%), thickening agent (from about 0% to about 5%), flavoring agent (from about 0.04% to about 2%), sweetening agent (from about 0.1% to about 3%), and surfactant (from about 0% to about 5%).

"Topical, oral carrier" as used herein, also denotes fibers, strips or tubes which can be impregnated with the halogenated amino acid derivative and inserted or implanted into a periodontal pocket. Such compositions of the subject invention can readily be achieved by one of ordinary skill in the art using the teachings disclosed hereinbefore, the following references hereby incorporated herein, and related well-known technologies: U.S. Pat. No. 4,666,897 issued to Golub, McNamara & Ramamurthy on May 19, 1987; European Patent Application No. 244,118 A1 in the name of Baker, published on Nov. 4, 1987; European Patent Application No. 286,802 A2 in the name of Kametaka, Miyazaki, Hayashi, Handa & Kameda, published Oct. 19, 1988; Addy, M., L. Rawle, R. Handley, H. Newman & J. Coventry, "The development and in vitro evaluation of acrylic strips and dialysis tubing for local drug delivery", *Journal of Periodontology*, Vol. 53 (1982), pp. 693–698; Goodson, J. M., A. D. Haffajee & S. S. Socransky, "Periodontal therapy by local delivery of tetracycline"- *Journal of Clinical Periodontology*, Vol. 6 (1979), pp. 83–92; Goodson, J., D. Holborow, R. Dunn, P. Hogan & S. Dunham, "Monolithic tetracycline containing fibers for controlled delivery to periodontal pockets", *Journal of Periodontology*, Vol. 54 (1983), pp. 575–579; Dunn, R., J. Gibson, B. Perkins, J. Goodson & L. Laufe, "Fibrous delivery systems for antimicrobial agents", *Polymer Science and Technology*, Vol. 32 (1985), pp. 47–59; Dunn, R., J. Gibson, B. Perkins, J. Goodson & L. Laufe, "Fibrous delivery systems for antimicrobial agents", *Polymer Material Science Engineering*, Vol. 51 (1984), pp. 28–31; Olanoff, L. & J. Anderson, "Controlled release of tetracycline—III: A physiological pharmacokinetic model of the pregnant rat", *Journal of Pharmacokinetics and Biopharmaceutics*, Vol. 8 (1980), pp. 599–620; Elkayam, R., M. Friedman, A. Stabholz, A. Soskolne, M. Sela & L. Golub, "Sustained release device containing minocycline for local treatment of periodontal disease", *Journal of Controlled Release*, Vol. 7 (1988), pp. 231–236; and Goodson, J., "Multi-center evaluation of tetracycline fiber therapy. I. Experimental Design", *Journal of Dental Research*, Vol. 68 (1989), p. 197; and references cited therein.

The pharmaceutically-acceptable carrier employed in conjunction with the compounds of the subject invention is used at a concentration sufficient to provide a practical size to dosage relationship, preferably constituting the entire portion of the compositions of the subject invention other than the halogenated amino acid derivative.

Total single dosages of the compositions of the subject invention are preferably as follows: for solid dose formulations, from about 1 mg to about 5 g, more preferably from about 10 mg to about 1 g, more preferably still from about 200 mg to about 1 g, and most preferably from about 250 mg to about 500 mg; for oral rinse, dentifrice and lozenge dose formulations, from about 0.1 mg to about 5 g, more preferably from about 1 mg to about 1 g, more preferably still from about 5 mg to about 500 mg, and most preferably from about 20 mg to about 100 mg; for impregnated fiber, strip or tube formulations, from about 0.001 mg to about 0.1 g, more preferably from about 0.01 mg to about 10 mg, and most preferably from about 0.05 mg to about 1 mg.

The following examples are typical of pharmaceutical compositions of the subject invention. The examples are not intended to be limiting of the variety and types of compositions contemplated herein. The composition are prepared using procedures well known in the tabletting and oral composition arts.

EXAMPLES 3–5

Tablet Compositions

| Ingredients | Example 3 (mg) | Example 4 (mg) | Example 5 (mg) |
|---|---|---|---|
| 3,6-Diamino-2-fluorohexanoic acid | 100 | 0 | 500 |
| N-(3-(S)-amino-2-(R)-fluorobutanoyl)glycine | 0 | 250 | 0 |
| Starch | 25 | 30 | 0 |
| Lactose | 40 | 20 | 0 |
| Mannitol | 0 | 0 | 20 |
| Talc | 0 | 0 | 25 |
| Colloidal Silicon Dioxide | 10 | 30 | 25 |
| Microcrystalline Cellulose | 10 | 10 | 20 |
| Carboxymethylcellulose | 10 | 20 | 40 |
| Stearic Acid | 3 | 5 | 10 |
| Magnesium Stearate | 1 | 3 | 0 |

EXAMPLES 6–8

Mouthrinse Compositions

| Ingredients | Example 6 (Wt. %) | Example 7 (Wt. %) | Example 8 (Wt. %) |
|---|---|---|---|
| 3,6-Diamino-2-fluorohexanoic acid | 0.1 | 0 | 1.0 |
| 3-Aminoacetamido-2-fluorobutanoic acid | 0.0 | 1.0 | 0.0 |
| Ethanol | 12.0 | 15.0 | 0 |
| Glycerin | 10.0 | 12.0 | 0 |
| Dibasic Sodium Phosphate Heptahydrate | 0.07 | 0.48 | 0 |
| Saccharin Sodium | 0.08 | 0.1 | 0.05 |
| Monobasic Sodium Phosphate Monohydrate | 2.03 | 1.82 | 0 |
| Polysorbate 80 | 0.33 | 0.33 | 0.25 |
| FD&C Blue (1% solution) | 0.02 | 0.02 | 0 |
| Flavor | 0.15 | 0.15 | 0.10 |
| Methylparaben | 0 | 0 | 0.20 |
| Propylparaben | 0 | 0 | 0.10 |
| Purified Water | qs | qs | qs |

EXAMPLES 9–11

Dentifrice Compositions

| Ingredients | Example 9 (Wt. %) | Example 10 (Wt. %) | Example 11 (Wt. %) |
|---|---|---|---|
| 3,6-Diamino-2-fluorohexanoic acid | 2.0 | 0 | 0 |
| 3-Aminoacetamido-2-fluorobutanoic acid | 0 | 3.0 | 0 |
| N-(3-(S)-amino-2-(R)- | 0 | 0 | 4.0 |

Dentifrice Compositions (continued)

| Ingredients | Example 9 (Wt. %) | Example 10 (Wt. %) | Example 11 (Wt. %) |
|---|---|---|---|
| fluoro-butanoyl)glycine | | | |
| Sorbitol | 42.0 | 40.0 | 37.0 |
| Sacchrin Sodium | 0.12 | 0.20 | 0.17 |
| FD&C Blue (1% solution) | 0.05 | 0.07 | 0.04 |
| Precipitated Silica | 20.0 | 0 | 23.0 |
| Alumina | 0 | 25.0 | 0 |
| Sodium Fluoride | 0.24 | 0 | 0.20 |
| Flavor | 0.90 | 1.50 | 1.20 |
| Sodium Alkyl Sulfate | 1.00 | 1.20 | 1.20 |
| Phosphoric acid | 0 | 0.40 | 0 |
| Carbomer 940 | 0.25 | 0.25 | 0.25 |
| Xanthan Gum | 0.65 | 0.50 | 0.60 |
| Titanium Dioxide | 0.50 | 0.50 | 0.50 |
| Purified water | qs | qs | qs |

EXAMPLES 12-14

Lozenge Compositions

| Ingredients | Example 12 (Wt. %) | Example 13 (Wt. %) | Example 14 (Wt. %) |
|---|---|---|---|
| 3,6-Diamino-2-fluorohexanoic acid | 1.0 | 0 | 0 |
| 3-Aminoacetamido-2-fluorobutanoic acid | 0 | 1.5 | 0 |
| N-(3-(S)-amino-2-(R)-fluoro-butanoyl)glycine | 0 | 0 | 3.0 |
| Sorbitol | 91.929 | 93.3893 | 69.4595 |
| Mannitol | 0 | 0 | 22.5 |
| Saccharin Sodium | 0.03 | 0.03 | 0.04 |
| FD&C Blue | 0.0005 | 0.0007 | 0.0004 |
| FD&C Yellow No. 6 | 0.0005 | 0 | 0.0001 |
| Flavor | 0.04 | 0.08 | 1.0 |
| Gum Crystal | 2.0 | 0 | 0 |
| Hydrogenated Vegetable Oil | 0 | 1.0 | 0 |
| Magnesium Stearate | 1.0 | 1.0 | 1.0 |
| Glycerol | 4.0 | 3.0 | 3.0 |

Another aspect of the subject invention is methods of using the compounds and compositions of the subject invention as described hereinbefore for prevention and/or treatment of various diseases or disorders caused by bacteria, especially anaerobic bacteria. The compounds and compositions of the subject invention can also be used alone or in conjunction with or as a component of cleaning compositions in order to disinfect and/or sterilize surfaces and articles. The compounds and compositions of the subject invention are useful for treatment of pseudomonas and other bacterial infections, especially in burns.

The compounds and compositions of the subject invention are particularly useful for the treatment or prevention of diseases and disorders caused by anaerobic bacteria. The compounds and compositions of the subject invention are especially useful against those caused by anaerobic bacterial infections involving tissues of external mucous memberane and mucocutaneous orifices. Non-limiting examples of anaerobic infections which may be treated by topical treatment methods of the subject invention include anaerobic infections of the skin or soft tissue (e.g., acne, gas gangrene, perirectal abscess, breast abscess, dermatological lesions, wound infections), the vagina (e.g., vulvovaginal abscess), the uterus (e.g., uterine infection), and diseases of the oral cavity (e.g., Vincent's disease, gingivitis, periodontal disease, dental abscess, infectious stomatitis). Non-limiting examples of anaerobic bacterial infections which are particularly suited for treatment by enteral or systemic treatment with the antibacterial agents of the subject invention include abdominal infections, cardiovascular infections, lung infections and intestinal infections. Specific anaerobe infections are more fully disclosed in Finegold's *Anaerobic Bacteria in Human Disease*, (Academic Press, Inc., New York, 1977) and in *Anaerobic Bacteria: Role in Disease* (published by Charles C. Thomas, Springfield, Ill.; Albert Balows, et al., editors; 1974), the disclosures of both of which are incorporated herein by reference.

When used to treat disorders or diseases caused by anaerobic bacteria, the daily dose of a compound of the subject invention is preferably from about 0.1 mg/kg to about 50 mg/kg, more preferably from about 0.5 mg/kg to about 20 mg/kg, more preferably still from about 1 mg/kg to 10 mg/kg, still more preferably from about 2 mg/kg to about 5 mg/kg.

The following examples are typical of methods of treatment or prevention of the subject invention. The examples are not intended to be limiting of the variety of methods contemplated herein.

EXAMPLE 15

For the treatment or prevention of gingivitis or periodontal disease, about 20 mL of the mouth rinse composition of Example 6 is used 2 times daily for 1 minute.

EXAMPLE 16

For the treatment or prevention of gingivitis or periodontal disease, the tablet composition of Example 5 is taken perorally 4 times daily.

EXAMPLE 17

For the treatment or prevention of gingivitis or periodontal disease, about 3 g of the dentifrice composition of Example 9 is applied to the teeth and gums with vigorous brushing 3 times daily for 2 minutes.

While particular embodiments of the subject invention have been described, it will be obvious to those skilled in the art that various changes and modifications of the subject invention can be made without departing from the spirit of the scope of the invention. It is intended to cover, in the appended claims, all such modifications that are within the scope of this invention.

What is claimed is:

1. A compound having the structure:

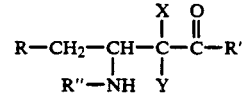

wherein —R is hydrogen or 2-aminoethyl; —R' is hydroxy, unsubstituted alkoxy, unsubstituted aryloxy, or an amino acid residue selected from the group consisting of glycyl, alanyl, arginyl, asparagyl, aspartyl, glutamyl, histidyl, leucyl, lysyl, methionyl, ornithyl, phenylalanyl, prolyl, sarcosyl, seryl, threonyl, tryptophyl, tyrosyl and valyl, the amino acid residue being bonded at the amino nitrogen; —R" is hydrogen or an amino acid residue selected from the group consisting of glycyl, alanyl, arginyl, asparagyl, aspartyl, glutamyl, histidyl, leucyl, lysyl, methionyl, ornithyl, phenylalanyl, prolyl, sarcosyl, seryl, threonyl, tryptophyl, tyrosyl and valyl, the amino acid residue being bonded at the carbonyl carbon; at least one of —R and —R" being other than hydrogen; —X is halogen; and —Y is hydrogen or halogen; and the pharmaceutically-acceptable salts thereof.

2. The compound of claim 1 wherein —R' is hydroxy or an amino acid residue.

3. The compound of claim 2 wherein —R' is hydroxy.

4. The compound of claim 3 wherein —R is 2-aminoethyl.

5. The compound of claim 4 wherein —R" is hydrogen.

6. The compound of claim 1 wherein —X is fluorine.

7. The compound of claim 3 wherein —X is fluorine.

8. A pharmaceutical composition comprising a compound of any of claims 1, 3, 5, 6 or 7 and a pharmaceutically-acceptable carrier.

9. A pharmaceutical composition comprising a compound of any of claims 1, 3, 5, 6 or 7 and a pharmaceutically-acceptable topical, oral carrier.

10. A method of treating diseases caused by anaerobic bacteria comprising administering to the oral cavity of a person in need of treatment a safe and effective amount of a compound of any of claims 1, 3, 5, 6 or 7.

11. A method of treating gingivitis or periodontal diseases caused by anaerobic bacteria comprising administering to the oral cavity of a person in need of treatment a safe and effective amount of a compound of any of claims 1, 3, 5, 6 or 7.

* * * * *

UNITED STATES PATENT AND TRADEMARK OFFICE
CERTIFICATE OF CORRECTION

PATENT NO. : 5,096,700

DATED : March 17, 1992

INVENTOR(S) : William L. Seibel and Joseph H. Gardner

It is certified that error appears in the above-identified patent and that said Letters Patent is hereby corrected as shown below:

Column 2, line 48, "2-carboxyl-th dine" should be
 --2-carboxyl-thiazolidine--.

Column 10, line 52, "a thickening agen about 0.1% to about 5%)" should be
 --a thickening agent (from about 0.1% to about 5%)--.

Signed and Sealed this

Twenty-second Day of February, 1994

*Attest:*

BRUCE LEHMAN

*Attesting Officer*    *Commissioner of Patents and Trademarks*